United States Patent [19]
Block et al.

[11] Patent Number: 5,532,124
[45] Date of Patent: Jul. 2, 1996

[54] GENETICALLY ENGINEERED BACTERIA TO IDENTIFY AND PRODUCE MEDICALLY IMPORTANT AGENTS

[75] Inventors: Timothy M. Block, Doylestown; Robert H. Grafstrom, Lansdowne, both of Pa.

[73] Assignee: Thomas Jefferson University, Philadelphia, Pa.

[21] Appl. No.: 98,313

[22] PCT Filed: Feb. 11, 1992

[86] PCT No.: PCT/US92/01188
§ 371 Date: Oct. 6, 1993
§ 102(e) Date: Oct. 6, 1993

[87] PCT Pub. No.: WO92/13972
PCT Pub. Date: Aug. 20, 1992

Related U.S. Application Data

[63] Continuation-in-part of Ser. No. 654,064, Feb. 11, 1991, abandoned.

[30] Foreign Application Priority Data

Oct. 4, 1991 [WO] WIPO ............ PCT/US91/07294

[51] Int. Cl.⁶ .................................................. C12Q 1/70
[52] U.S. Cl. .......................... 435/5; 435/6; 435/23; 435/34; 435/68.1; 435/69.1; 435/69.2; 435/184; 435/244; 435/252.3; 435/974
[58] Field of Search ................... 435/68.1, 69.1, 435/69.2, 243, 244, 252.3, 5, 23, 34, 6, 29, 184, 236, 238, 974; 514/2, 44

[56] References Cited

FOREIGN PATENT DOCUMENTS 0421109  4/1991  European Pat. Off. .

OTHER PUBLICATIONS

McCall et al, "A High Capacity Microbial Screen for Inhibitors of Human Rhinovirus Protease 3C" *Biotechnology*, vol. 12, (Oct. 1994), pp. 1012–1016.

Block et al "Novel Bacteriological Assay for Detection of Potential Antiviral Agents" *Antimicrobiological Agents & Chemoth* vol. 34, No. 12 pp. 2337–2341 (1990).

Debouck et al "Human immunodeficiency virus protease expressed in *E coli* exhibits autoprocessing & specific maturation of the gag precursor" *PNAS* vol. 84 pp. 8903–8906 (Dec. 1987).

Moore et al "Peptide Substrates & Inhibitors of the HIV–1 Protease" *Biochem & Biophys Research Com* vol. 159, No. 2 pp. 420–425 (Mar. 15, 1989).

Barany "Two–codon insertion mutagenesis of plasmid genes by using single–stranded hexameric oligonucleotides" *PNAS* vol. 82 pp. 4202–4206 (Jun. 1985).

*Primary Examiner*—Christine M. Nucker
*Assistant Examiner*—Jeffrey Stucker
*Attorney, Agent, or Firm*—Woodcock Washburn Kurtz Mackiewicz & Norris

[57] ABSTRACT

Microorganisms modified such that their growth in selective media is dependent upon the inhibition of a medically important target function are provided and utilized in methods for the screening of potential medically important compounds.

11 Claims, 6 Drawing Sheets

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
( A ) LENGTH: 7
( B ) TYPE: amino acid
( D ) TOPOLOGY: linear ( x i ) SEQUENCE DESCRIPTION: SEQ ID NO:1:

Ser Gln Asn Tyr Pro Ile Val
1               5

( 2 ) INFORMATION FOR SEQ ID NO:2:

( i ) SEQUENCE CHARACTERISTICS:
( A ) LENGTH: 7
( B ) TYPE: amino acid
( D ) TOPOLOGY: linear ( x i ) SEQUENCE DESCRIPTION: SEQ ID NO:2:

Ser Ser Pro Ser Pro Ser Gln ( 2 ) INFORMATION FOR SEQ ID NO:3:

( i ) SEQUENCE CHARACTERISTICS:
        ( A ) LENGTH: 15
        ( B ) TYPE: nucleic acid
        ( C ) STRANDEDNESS: single
        ( D ) TOPOLOGY: linear ( i v ) ANTI-SENSE: no ( x i ) SEQUENCE DESCRIPTION: SEQ ID NO:3:

ATCGTCNNNN YCGRC 15

( 2 ) INFORMATION FOR SEQ ID NO:4:

( i ) SEQUENCE CHARACTERISTICS:
        ( A ) LENGTH: 5
        ( B ) TYPE: amino acid
        ( D ) TOPOLOGY: linear ( x i ) SEQUENCE DESCRIPTION: SEQ ID NO:4:

Cys Met Ala Phe Pro
        1                 5

( 2 ) INFORMATION FOR SEQ ID NO:5:

( i ) SEQUENCE CHARACTERISTICS:
        ( A ) LENGTH: 12
        ( B ) TYPE: amino acid
        ( D ) TOPOLOGY: linear ( x i ) SEQUENCE DESCRIPTION: SEQ ID NO:5:

Met Lys Arg Pro Pro Gly Phe Ser Phe Arg Ser Val
        1               5                    10

( 2 ) INFORMATION FOR SEQ ID NO:6:

( i ) SEQUENCE CHARACTERISTICS:
        ( A ) LENGTH: 7
        ( B ) TYPE: amino acid
        ( D ) TOPOLOGY: linear ( x i ) SEQUENCE DESCRIPTION: SEQ ID NO:6:

Met Lys Arg Pro Pro Gly Phe
        1               5

( 2 ) INFORMATION FOR SEQ ID NO:7:

( i ) SEQUENCE CHARACTERISTICS:
        ( A ) LENGTH: 8
        ( B ) TYPE: amino acid
        ( D ) TOPOLOGY: linear ( x i ) SEQUENCE DESCRIPTION: SEQ ID NO:7:

Pro Gly Phe Ser Phe Arg Ser Val
        1               5

( 2 ) INFORMATION FOR SEQ ID NO:8:

( i ) SEQUENCE CHARACTERISTICS:
        ( A ) LENGTH: 7
        ( B ) TYPE: amino acid
        ( D ) TOPOLOGY: linear ( x i ) SEQUENCE DESCRIPTION: SEQ ID NO:8:

Phe His Leu Leu Val Tyr Ser (2) INFORMATION FOR SEQ ID NO:9:

(i) SEQUENCE CHARACTERISTICS:
        (A) LENGTH: 7
        (B) TYPE: amino acid
        (D) TOPOLOGY: linear (xi) SEQUENCE DESCRIPTION: SEQ ID NO:9:

```
Tyr  Ile  His  Pro  Phe  His  Leu
 1                    5
```

(2) INFORMATION FOR SEQ ID NO:10:

(i) SEQUENCE CHARACTERISTICS:
        (A) LENGTH: 69
        (B) TYPE: nucleic acid
        (C) STRANDEDNESS: single
        (D) TOPOLOGY: linear (iv) ANTI-SENSE: no (xi) SEQUENCE DESCRIPTION: SEQ ID NO:10:

```
AATTCTTGTA  CATGTCCCAC  TGTTCAAGCC  TCCAAGCTGT  GCCTTGGGTG   50

GCTTTGGGGC  ATGGACATA                                        69
```

GENETICALLY ENGINEERED BACTERIA TO IDENTIFY AND PRODUCE MEDICALLY IMPORTANT AGENTS

REFERENCE TO RELATED APPLICATION

This application is a continuation-in-part of U.S. application Ser. No. 07/654,064, filed Feb. 11, 1991, now abandoned.

BACKGROUND OF THE INVENTION

Chemotherapeutic intervention has been a bulwark of modern medicine. Treatment of cancer, hypertension, heart disease, inflammation and endocrine disorders are just a few examples of human disorders, some of them life threatening, which have been successfully managed or cured by drugs alone or in combination with other therapy. Infectious diseases caused by bacteria, fungi and parasites have also been successfully managed or cured by drug therapy.

Central to the discovery of new medically effective drugs is the ability to screen for effective agents and identify sources of their production. It is safe to say that the ability to screen and locate important compounds is often the limiting step in the discovery of these agents. Current assays for drugs used in the treatment of hypertension and inflammation, for example, often require the use of unpredictable enzyme and cellular assays. Similarly, the detection of drugs that are effective against viruses often require sophisticated and cumbersome cell culture or virus enzyme assays. These assays are not often amenable to high volume studies, and most crude samples of impure compounds or crude extracts of natural products, which are often the source of effective drugs, cannot be tested in these assays without considerable prior purification.

In addition, the discovery of effective drugs depends either upon the large scale screening of thousands of different compounds or the reasoned design of drugs that, by their structure, are predicted to be effective. This approach has been, to date, the only means of drug discovery.

Much attention has focused on the discovery of therapeutic agents effective against Human Immunodeficiency Virus (HIV). HIV is the causative agent of the human disease, Acquired Immunodeficiency Syndrome (AIDS) and AIDS Related Complex (ARC). These are devastating illnesses that represent a major worldwide health threat. HIV is a member of the RNA genome-containing retroviruses and requires the function of virally specified gag and reverse transcriptase (pol) polypeptides. As with other RNA tumor viruses, the HIV life cycle involves synthesis of a double stranded DNA copy of the genomic RNA. This process is catalyzed by the viral reverse transcriptase, and inhibition of this enzyme inhibits virus replication.

Dependency of HIV upon unique virally encoded functions, such as the reverse transcriptase, presented the possibility of rationally designing antiviral agents to be directed towards interfering with those functions. For example, the nucleotide analog azidothymidine (AZT) is an effective anti-HIV agent and is presumed to work by forming chain terminating products generated by retroviral reverse transcriptase. It should therefore be possible to impede or prevent virus growth by developing pharmacological agents that inhibit essential virus functions.

The gag and pol proteins perform essential HIV retroviral functions. Mature gag and pol products are derived from the proteolytic processing of polypeptide precursors. This proteolytic cleavage is mediated by a virally specified protease that is essential for virus growth. Inhibition of this viral protease is therefore likely to prevent HIV maturation.

There is enormous interest in the discovery of HIV protease inhibitors present as natural products or derived from chemical synthesis. Each candidate inhibitor must be tested for its ability to prevent HIV protease from enzymatically cleaving substrates such as preparations of either gag-pol precursors or synthetic oligopeptides containing the HIV protease recognition sequence. Such assays are time consuming and costly, usually involving separation of cleaved products by electrophoresis or other methods of chromatography, such as HPLC. All of these methods require a reasonable degree of technical sophistication. The search for an effective HIV protease inhibitor would be greatly assisted by the availability of a simple, rapid and inexpensive assay.

Similarly, it is critical that a rapid screening assay for inhibitors of HBV be developed. HBV-is associated with chronic liver disease, including chronic hepatitis, cirrhosis and hepatocellular carcinoma. Infection with HBV can lead to one, or a combination, of the following outcomes: inapparent infection followed by seroconversion, acute hepatitis followed by recovery or death, and chronic infection. Chronically infected individuals possess HBV genetic information in their hepatocytes and often experience persistent viremia with an absence of neutralizing antibodies. These individuals may experience no frank symptoms and may carry the virus in their livers, and possibly elsewhere, for a period of years.

Twenty to forty percent of all chronic carriers will eventually die from serious liver disease, including cirrhosis and primary liver cancer. Although the precise mechanisms of these clinical endpoints are not known, these outcomes are believed to be the result of HBV infection. There is no question that HBV is associated with serious liver pathology and the use of antiviral agents in the treatment of HBV infection should be of great value.

The epidemiology of HBV indicates a worldwide problem. More than 250,000,000 people are chronic carriers of HBV. As many as 100,000,000 of these people can be expected to die prematurely from serious liver disease. Most of these people will be afflicted and require hospitalization during the most productive period of their early-mid adulthood. It is evident that a cure for HBV induced disease will relieve great suffering.

Although there is an effective vaccine to prevent HBV infection from establishing chronic infection, there is currently no effective therapy for the hundreds of millions of people infected. Recently, alpha interferon has been shown to be useful in 10–25% of adults recently infected. Although it is not helpful in those who have been infected at birth, the vast majority of carriers, the promising results of alpha interferon underscore the potential of anti-HBV therapies.

Currently, assays for the detection of anti-HBV agents are limited. Animal models of HBV, including woodchuck hepatitis (WHV) and duck hepatitis viruses (DHBV), have been of enormous value in the virological study and assay of potential chemotherapeutic agents. However, animal experiments are expensive and time consuming. Therefore, the large scale investigation of many different compounds using such methods is not practical and the assay of crude mixtures of materials is not reasonable. Further, tissue culture systems for the propagation of hepatitis viruses have been reported. Such systems are likely to prove to be of considerable value. However, even tissue cultures are delicate and those described are of very limited efficiency. Since HBV grows poorly in tissue culture and biochemical assays for the two known virally specified enzymes are complicated, the pursuit of antiviral agents has been limited. Other virus systems have benefited from the development of biochemical assays for virus-specific enzymes. At present, it is difficult to impossible to assay HBV-specific enzymes in the absence of infected cell material or partially pure virions. Clearly, HBV antiviral research would benefit from more simple, rapid and specific assays.

There is also a global need for the identification and selection of inhibitors of members of the Herpes virus family. Herpes viruses are ubiquitous and are the causative agents of a wide range of opportunistic human diseases. They are among the leading causes of non-trauma induced blindness, encephalitis, sexually transmitted diseases, and morbidity in immunocompromised hosts.

Since the isolation of antibiotics, interest in bacteria both as the source of biologically important molecules and as a solution to environmental problems has been a leading impetus for the study of these organisms. In addition to the hundreds of antibiotics, the anticancer agent, adriamycin, the antiviral agent, adenosine arabinoside, and the immune modulator, cyclosporin A have all been isolated from microorganisms. Recently, bacteria with other special properties such as the ability to dissolve oil spills or to prevent frost formation on crops have been important additions to the repertoire of useful bacteria. With the advent of recombinant DNA techniques it became clear that recombinant bacteria could also be turned into a factories for producing new and useful drugs that could not otherwise be readily synthesized in the laboratory. These drugs include such well known proteins as insulin, growth hormone and clotting factor. The use of recombinant bacteria has also been invaluable in the study of clinically important bacteria and viruses. These efforts have increased the safety of studying very hazardous organisms, and have allowed for the production high levels of proteins necessary for both biochemical studies and safe vaccines. Moreover, recombinant bacteria have the capacity to internalize a broad spectrum of chemical classes many of which are also taken up by mammalian cells.

The "AMES" test for mutagens has proven to be a useful predictor of the carcinogenic potential of many chemicals. (Ames et al., 1975, Methods For Detecting Carcinogens And Mutagens With *The Salmonella*/Mammalian-Microsome Mutagenicity Test, *Mutat. Res.*, 32:347–364). This assay exploits the rapid and inexpensive growth of bacteria to test the ability of test compounds to cause mutations. The invention described herein utilizes a rapid bacteriologically based bioassay to test pharmacological compounds for their ability to inhibit activities of a plethora a gene products associated with disease states, such as proteins elaborated by viral and pathological endogenous genes.

EPO Publication No. 0 421 109 A2 (Baum et al.) also discloses a method for screening compounds which inhibit protease utilizing *E. coli* transformed with β-galactosidase which is capable of being assayed by reacting with a color indicator compound to produce a color change. In this method, a DNA sequence encoding a peptide sequence recognized by HIV or polio 3C protease was inserted into the β-galactosidase gene, and this chimeric construct was transformed into an *E. coli* strain, along with an HIV or polio 3C protease gene. Growth of recombinant organisms was carried out in a nutrient medium containing the chromogenic compound and a potential protease inhibitor compound. If the test compound inhibits the protease, the expression system produces an intact chimeric β-galactosidase, and color is maintained in the assay system. If the compound is not an inhibitor, the protease cleaves the protease enzyme cleavage site of the peptide, the reporter protein is inactivated and no color is observed in the assay system.

The instant invention provides a method in which dominant selectable markers are used for the selection of mutant microorganisms which may themselves be producing valuable compounds or possess valuable mutations. Unlike Baum et al., the present invention may utilize a chromogenic or non-chromogenic indicator compound and thus has greater utility. Further, nowhere in Baum et al. is it disclosed that the tetracycline resistance protein, which is useful in the instant invention, can be used as the reporter protein. Additionally, the method of Baum et al. is limited to the insertion of an HIV or 3C protease cleavage site sequence into the β-galactosidase gene. There remains a need for rapid, simple and inexpensive methods to identify and isolate viral inhibitors and other medically important agents.

SUMMARY OF THE INVENTION

The present invention relates to a novel method to identify antiviral and other medically important agents. The present invention provides a method of identifying a medically important drug comprising providing a microorganism expressing both a medically important target and a modified reporter function such that the reporter function may be deactivated by the medically important target; adding a test compound to the culture medium containing the microorganism; adding an selection agent to the culture medium; culturing the microorganism; and observing the growth of the microorganism in the culture medium.

Embodiments provide methods of identification and isolation of microorganisms that produce medically important agents. For example, anti-HIV, anti-HBV or anti-herpes activity or other medically important agents or activities can be identified and isolated.

Other embodiments of the present invention provide methods for characterization of organisms expressing a modified reporter gene.

The present invention has several advantages over in vitro biochemical assays for antiviral agents and other medically important compounds. First, crude mixtures of chemical compounds that might otherwise nonspecifically inhibit in vitro biochemical or cellular assays can be screened. Second, the invention may be generally applied. For example, methods of the invention include, but are not limited to, medically important targets such as HIV protease, HBV x kinase, HSV α4 protein, renin, angiotensin, and kallikrein. Third, mutant microorganisms that grow in the presence of selection agent can be detected; they will provide important information about the medically important targets as well as the selecting or indicating agent. Finally, among these mutants there may be ones that synthesize novel inhibitors of medically important targets.

Methods for the identification of drugs and selection of microorganisms that produce inhibitors of HIV protease, HBV x kinase, HSV α4 protein, and HBV pregenome packaging; mediators of high blood pressure and mediators of inflammation are also provided.

DETAILED DESCRIPTION OF THE INVENTION

Figure 1:
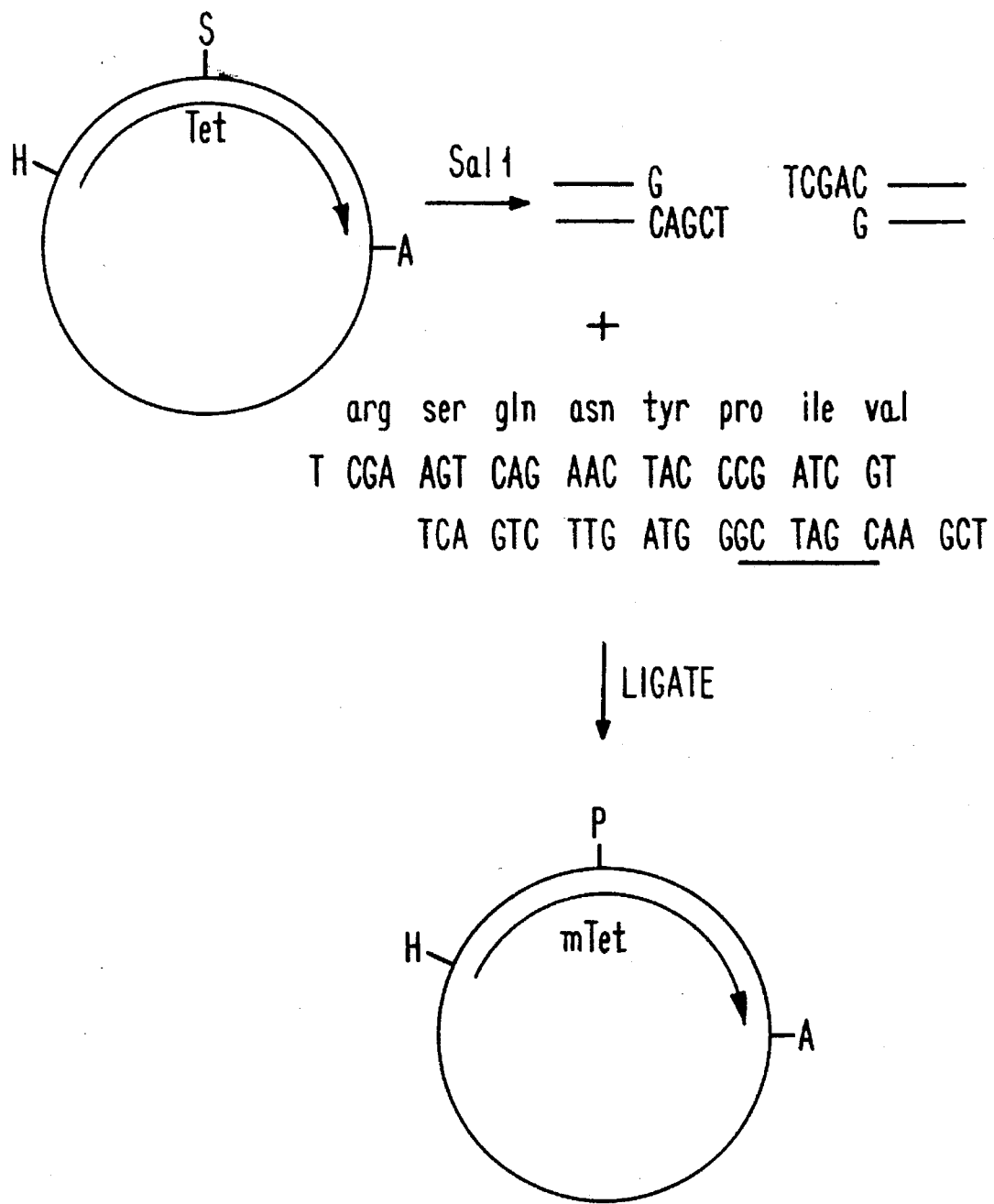
FIG. 1 is a diagram showing the construction of the Tet protein containing an HIV protease cleavage site. A 24-bp synthetic oligonucleotide was inserted into the SalI (S) site of the tet gene, destroying the SalI site but providing a new PvuI (P) site (underlined). This new construct containing the Tet protein with the HIV protease site was called pACYC-10B3; H=HindIII and A=AvaI.

The present invention provides novel methods for the screening for medically important drugs, as well as the identification, selection and characterization of microorganisms that may themselves be producing medically important compounds.

Generally, the present invention provides for large scale screening for medically useful drugs microorganism-based methods. Genetically engineered microorganisms are used which will preferentially grow or turn color when a medically useful drug is present. Therefore, assays can be done simply and in high volume at minimal expense as unsophisticated microorganism growth studies. Even crude and impure compounds can be tested with the genetically engineered microorganism. If a compound is of potential value, growth of the microorganism is enhanced or in another embodiment, the color of the microorganism changes.

Means of selecting and isolating microorganisms which produce medically important drugs are also provided by the present invention. Genetically altered microorganisms, which can grow in selective medium when medically important targets are inhibited, are constructed. The genetically altered microorganisms are placed in selective medium containing a selection agent. Most of the microorganisms will not grow in selective medium. Rare mutants will arise, however, and can be isolated. Some of these mutants are expected to arise because they themselves are producing medically important compounds. These mutants are tested for the possibility that they are producing a medically important compound. If they do produce such, the medically important compound will be isolated and characterized. Moreover, methods of the present invention provide sources for the continuous production of the medically important compounds because the compounds are derived from a regenerating microorganism which can continuously supply them.

The present invention described general methods for the use of microorganisms for the screening for any medically important drug. Bacteria, yeast and other microorganisms may be useful in the present invention. The present invention also provides general methods for the use of microorganisms in the selection of mutant microorganisms which may themselves be producing medically important compounds. The methods require that the microorganisms be genetically engineered such that they contain the gene for a medically important target and that their growth on selection medium requires that the function of this medically important target be inhibited. That is, the only way that the genetically altered microorganism can grow on the selection media is if the function of the medically important target is inhibited.: Another embodiment of the invention provides that the color of an indictor changes when a medically important target of a genetically altered microorganism is inhibited.

Herein, the term "medically important target" refers to the target of drugs that are of therapeutic value. Examples of medically important targets are human enzymes involved in the process of blood pressure control such as renin and angiotensin converting enzyme (ACE); enzymes involved in the control of inflammation such as kallikrein(s); enzymes involved in the processing and growth of human viruses such as the HIV protease and HBV x kinase; regulatory proteins involved in the growth of cancer cells or human viruses such as herpes simplex virus (HSV) α4; and other functional proteins and organic molecules.

To be useful in the pursuit of medically important compounds, the gene encoding the medically important target may be molecularly cloned into the microorganism in such a manner that its expression can be induced; the gene product of the medically important target must be functional in the genetically altered microorganism; and, selection medium must be available or constructed that is either inhibitory to the growth of the genetically altered microorganism when the medically important target is expressed, or changes color when the genetically altered microorganism is grown. The invention provides methods for screening of inhibitors of medically important targets, as well as methods for the selection of mutants of genetically altered microorganisms that may themselves be producing inhibitors of medically important targets.

Demonstrations are provided where the method was used in the construction of *E. coli* strains that are useful for the detection of inhibitors of the following medically important targets: HIV protease, HSV α4, DNA binding protein, HBV x kinase, HBV packaging function. Other examples of medically important targets for which designs are provided are: kallikrein, a mediator of inflammatory responses; and, renin and angiotensin converting enzyme (ACE), mediators of hypertension. The examples provided range from antiviral to antiinflammatory agents and involve very different viral and cellular functions showing that the invention can be applied to many different medically important targets. The method described in this invention can be used for the detection of inhibitors and modifiers of any medically important target that can be expressed in microorganisms and render the host cell dysfunctional. Moreover, with these modified microorganisms it is possible to select mutants which may themselves be producing an important inhibitor or modifying agent.

One embodiment of the present invention is an assay for the initial screening of potential medically important compounds. The invention relates to methods of identifying medically important agents and methods of identification and isolation of microorganisms that produce medically important agents. Methods of identifying a medically important agent comprising providing a microorganism, such as a bacteria or yeast, expressing both a medically important target and a modified reporter function such that the reporter function may be deactivated by the medically important target; adding a test compound to the culture medium containing the microorganism; adding selection agent to the culture medium; culturing the microorganism; and observing the growth or color change of the microorganism in the culture medium. Growth or color change of the organism indicates that the test compound may be a medically important agent. Selection agents provided by the present invention include, for example, traditional selection agents, such as antibiotics, and indicating compounds, such as those detectable through changes in the media. Herein, the "selection media" refers to culture medium containing selection agent.

Another embodiment of the present invention provides methods of identification and isolation of microorganisms that produce medically important agents comprising providing microorganisms, for example, yeast or bacteria, expressing both a medically important target and a modified reporter function such that the reporter function may be deactivated by the medically important target; adding selection agent to the culture medium containing the microorganisms; observing the growth of the microorganisms; and isolating selected organisms with a medically important activity, for example, anti-HIV, anti-HBV or anti-herpes activity or other medically important activity. Growth of the organism indicates that the organism may be expressing or elaborating a medically important agent.

Another embodiment of the present invention provides methods for characterization of organisms expressing a modified reporter function comprising isolating the genetic information comprising the modified reporter function from the mutant; reintroducing the genetic information into a host to derive transformants; selecting transformants derived by adding a selection agent to the culture medium containing the microorganism; and observing the growth of selected transformants in the culture medium. Growth of the organism indicates that the organism may be expressing or elaborating a medically important agent.

The present invention also includes a further embodiment used for characterization of mutants expressing a modified reporter function comprising isolating organisms expressing modified reporter function; adding the organisms expressing modified reporter function to organisms expressing both a medically important target and a modified reporter function in a culture medium such that the reporter function may be deactivated by the medically important target; adding selection agent to the culture medium; and, selecting microorganisms expressing modified reporter function that promote the growth of organisms expressing both a medically important target and a modified reporter function.

In accordance with the teachings of this invention, a microorganism whose growth media containing selection agent is dependent upon the inhibition of a medically important targets, such as a vital viral function, is constructed. To demonstrate the invention, HIV protease was chosen.

HIV protease is essential for the growth of the virus. Compounds that inhibit the activity of this protease may have therapeutic value in the treatment of diseases caused by HIV such as AIDS and ARC. The rapid, inexpensive and easy evaluation of drugs that may inhibit the HIV protease is therefore of critical importance.

HIV structural and replicative proteins are generated from a larger precursor polyprotein by viral protease. Cellular proteases do not cleave the Pr55 gag and Pr160 gag-pol polyproteins. HIV protease cleaves at the Tyr-Pro peptide bond and recombinant protease produced in *E. coli* is functional and can cleave the heptapeptide Ser-Gln-Asn-Tyr-Pro-Ile-Val, SEQ ID NO: 1, in vitro. Since mutant viruses that lack the protease function are defective, this enzyme has been recognized as an excellent target for antiviral therapy.

In order to construct a bacterial strain whose growth depends upon agents that inhibit HIV protease, the bacterial target protein must be essential for bacterial growth and contain a susceptible HIV protease recognition sequence. The Tet protein mediates resistance to tetracycline by preventing its intracellular accumulation. It contains two functional domains, TetA and TetB, separated by a short hinge region. Previous mutational analysis of the *E. coli* pBR322 tet gene demonstrated that two additional amino acids could be inserted into the hinge region without a significant loss in tetracycline resistance. Consequently, the HIV protease recognition sequence was inserted into this hinge region of the Tet protein. This modification causes the tetracycline resistance protein to be a substrate for the HIV protease within the cell. Thus, the mutability of the Tet protein and the availability of stringent selections for its phenotype made it a useful target for the HIV protease and for the demonstration of the invention. *E. coli* were transformed to contain plasmids encoding and expressing functional HIV protease genes as well as an altered tetracycline or other antibiotic resistance gene.

Cells expressing both the altered tetracycline resistance and HIV protease genes will not grow in the presence of tetracycline, since the tetracycline resistance protein will be degraded. Test compounds are added to the growth medium and, if the HIV protease is inhibited, bacteria grow and the agent can be evaluated further. Large numbers of compounds may be tested quickly and inexpensively using the methods of the invention. Relatively unskilled individuals will be able to conduct the tests with a minimum of complicated equipment. This can be particularly important in the primary screening of natural products at the site of the isolation.

In another embodiment, these altered bacteria allow for the selection of bacteria that produce inhibitors of the HIV protease. The altered bacteria can be cultured in the presence of tetracycline. Most of the plated organisms will be killed, since the altered bacteria expresses a Tet protein that is degraded by the HIV protease. Rare variants arise, however, because of mutations in either the Tet protein, or HIV protease, or because of production by the bacteria of inhibitors of the HIV protease. Some of these mutants are expected to be useful in the production of novel protease inhibitors.

A still further embodiment of the present invention is where a microorganism is constructed that expresses functional HIV Tat gene product and a dominant selectable marker or reporter gene mRNA containing the Tar sequence. The Tar sequence is recognized by Tat and may be positioned at various sites in the transcript thereby interfering with expression of the selectable marker.

The present invention also includes using Trp auxotroph bacterial strains, different bacterial genera, or yeast, to exploit alternative ways that microorganisms can devise to inhibit the HIV protease or other critical viral functions.

In another embodiment of the present invention, a bacteriological assay for the detection and generation of HBV antiviral agents is provided. The concept behind this embodiment is essentially similar to that described for the HIV system, constructing a bacterial strain that expresses a vital virus function and whose growth in selective media depends upon the inhibition of that function.

In a preferred embodiment of the present invention the x kinase (hbx) can used as a target since it serves a vital viral function. HBV is a small incompletely double stranded DNA virus with a distinct liver tropism and a complicated life cycle. Expression of the viral genome is modulated by liver specific enhancers and it codes for at least four gene products (core, pol, S and x), which are produced from overlapping genes. All hepadnaviruses appear to use a RNA replication intermediate as a template for their minus DNA strand synthesis and have been shown to induce a virus specific reverse transcriptase. HBV is believed to encode only two distinct enzymatic activities: the virus polymerase, which is a reverse transcriptase, and a transcriptional activator with protein kinase activity. These are the products of the pol and x genes, respectively.

The x gene encodes a 16.5 kd protein and is an ideal target for the selection of antiviral agents. It has been molecularly cloned in *E. coli* and shown to have the transcriptional activation activity with which the native gene product is associated. The x protein has also been shown to be a protein kinase with serine and threonine specificity (Wu et al. 1990, Cell, 63: 687–695). Moreover, this kinase activity was recovered from the bacterially produced enzyme.

The importance of the x gene to oncogenesis, and its attractiveness as a target for antiviral therapy, are underscored by the following points. First, all known oncogenic HBV-like viruses possess an x gene, whereas the non-oncogenic DHBV does not. HBV viruses that are mutant in x function are growth defective. Recently, x gene expression in transgenic mice was associated with malignant transformation of primary liver cells, suggesting that overexpression of the x gene, alone, was associated with the oncogenic process. Finally, since the x gene is virus-specific and mutants lacking the x gene are growth defective in vivo, compounds active against the x function may show anti-HBV specificity and effectiveness.

The present invention provides that bacteria will be constructed that express the x gene. Such recombinant bacteria will be transformed to elaborate a Tet efflux protein that has been modified to contain the amino acid recognition sequence that is a substrate for the x kinase. Based on previous studies a likely recognition sequence for autophosphorylation is Ser-Ser-Pro-Ser-Pro-Ser-Gln, SEQ ID NO: 2. Herein, the modified tetracycline resistance gene is referred to as tet-x. It is believed that the Tet efflux protein, containing the amino acid recognition site for the x kinase will become phosphorylated by the x kinase within the bacterial cell. Since the Tet efflux protein is a membrane protein responsible for conferring resistance to tetracycline, it is further believed that phosphorylated Tet proteins will not be functional. Thus, bacteria expressing both the x protein and phosphorylated Tet protein will be tetracycline sensitive. An example of such bacterial strains is called TJU-hbx:$tet^x$.

Inhibitors of the hbx kinase will be detected by co-cultivation with TJU-hbx:$tet^x$. Agents that inhibit hbx will be recognized by their ability to enhance the growth of the bacteria in tetracycline media. Since this is a positive growth assay wherein positives cause growth, not death, of the bacteria, false positives that nonspecifically kill *E. coli* will not be a complication. Agents that appear promising in this assay can than be promoted to further rigorous analysis in other conventional tissue culture tests. Optimum assay conditions will be determined by one skilled in the art. Methods for the co-cultivation of this strain with candidate compounds and mixtures will be developed. This should be straightforward to one skilled in the art by testing of compounds for their ability to enhance growth of this strain in tetracycline. Crude compounds derived from plant extracts, chemical mixtures and soil samples will be co-cultivated with the strain. Any mixture observed to consistently elevate the growth of this strain, and not affect hbx minus strains, will be examined. For example, crude mixtures will be fractionated by whatever separation methods are appropriate for the source, and retested by the co-cultivation assay. Fractions exhibiting positive growth effects will be further resolved by chromatography and monitored for activity in the bacterial growth assay. When the compound is believed to be sufficiently enriched and pure, it will be tested directly for its ability to: inhibit the hbx kinase in the conventional kinase assay; and, inhibit the growth of HBV in tissue culture. This bacteriological assay will allow one to screen many compounds from a range of sources that would not be possible to test in other systems.

Prototype strain *E. coli* TJU-hbx:$tet^x$ has been constructed and analyzed to demonstrate an embodiment of the invention. As expected, this strain is unable to grow in a tetracycline containing media under conditions where the hbv x gene is induced. Such results demonstrate the usefulness of this embodiment of the present invention.

Although TJU-hbx:$tet^x$ is unable to thrive on agar plates containing tetracycline, under conditions of hbx gene product induction, it is believed that rare viable variants will emerge at a frequency of approximately 1 in 10,000. These mutants will be isolated and are expected to belong to the following classes: those that have an altered tetracycline metabolism; those that have deleted the x gene sequence or have lost the ability to express the x gene; those that have altered the Tet-x protein or its expression level; and, those that produce an inhibitor of the hbx kinase.

It will be necessary to be able to easily distinguish one class of mutants from the other to decide which mutants are the most useful as antiviral compounds. Straightforward genetic and biochemical strategies for categorizing mutants as they arise are included in the present invention. The classification strategy, briefly, involves determining if the mutation lies within the host chromosome or plasmids. If the mutation lies within the host chromosome, it will be examined further for the possibility that they produce an inhibitor of hbx. For example, material from such mutants will be tested for the ability to enhance the growth of either TJU-hbx:tet$^x$ under induction of hbx conditions or tet-x (lacking hbx) strains in tetracycline media. If such material enhances only the growth of TJU-hbx:tet$^x$ strains, but not tet-x, it will be considered very likely that the mutant bacteria is producing an inhibitor of hbx. Such mutants will be pursued for characterization and isolation by both the bacteriological and biochemical assays used by those skilled in the art. Such assays will include, for example, kinase assays.

Mutants that possess altered Tet metabolism, x gene lesions, or altered Tet-x protein or expression, will also be fully characterized because they will reveal useful genetic or structural information about tetracycline metabolism or hbx function.

The present invention provides that cell wall-less strains or gram positive bacteria may be adapted to the methods described if transport of putative compounds is believed to be a problem. Moreover, with appropriate adaptation by one skilled in the art, the bacterial assay could be made to be quantitative.

Another embodiment provides strains of *E. coli* that express functional HBV core protein as well as a modified tetracycline resistance mRNA gene product. The modified tet mRNA contains the 64 nucleotide pac site recognized by HBV core and pol gene products. (Junker-Neipmahn et al., *EMBO J.*, 9:3389–96 (1990)). It has been previously shown that the HBV core and pol gene products will package, or complex with, mRNA that contains the 64 nucleotide consensus sequence of the 85 nt pac site. (Junker-Neipmahn et al., *EMBO J.*, 9:3389–96 (1990)) The conserved sequence to be used is: AAT TCT TGT ACA TGT CCC ACT GTT CAA GCC TCC AAG CTG TGC CTT GGG TGG CTT TGG GGC ATG GAC ATA, SEQ ID NO: 10. Packaging of HBV pregenomic RNA in to virions is an essential step in the production of infectious virus. It is believed that drugs which inhibit the packaging process will be of value in the management of chronic HBV infection. It is further believed that bacteria expressing functional HBV core and pol proteins, as well as a tet mRNA that contains the 64 nucleotide pac site, will be unable to grow in tetracycline media. Growth will be halted in these strains because the tet mRNA will be packaged or otherwise complexed with pol and core protein, and will be not be translated into Tet protein. Bacteria containing the modified tet mRNA and core proteins can be further transformed to contain plasmids that express the HBV pol gene product. *E. coli strain TJU-HBV-core*1-pol1:tet has been constructed and possesses the sensitivity to tetracycline under induction of the core and pol genes that is expected.

Another embodiment of the present invention provides construction of bacteria that can only grow in tetracycline media when the human enzyme Kallikrein is inhibited.

A further embodiment of the invention provides construction of bacteria that can only grow in tetracycline when the human enzyme renin is inhibited.

A still further embodiment of the invention provides construction of a bacteria that can only grow in tetracycline when the human enzyme angiotensin converting enzyme is inhibited.

Additional embodiments of the present invention include bacterial strains that possesses an antibiotic resistance gene containing DNA binding sequences recognized by a medically important DNA binding protein, including viral DNA binding proteins. The present invention provides that these binding sites be located within the control regions or coding regions of the resistance gene and that the expression of the medically important DNA binding protein prevents the expression of the antibiotic resistance gene. It is further provided that agents that inhibit the ability of the medically important DNA binding protein to function will restore the ability of the bacteria to grow in the selected antibiotic. It is expected that many variations of the aforementioned methods of the invention to discover medically important drugs targeting medically important DNA binding proteins, may be easily be determined by one skilled in the art.

A preferred embodiment of the present invention provides the construction a bacterial strain whose growth in selective media depends upon the inhibition of the DNA binding activity of the HSV α4 protein, which is essential for virus growth. The function of α4 appears to be conserved in the phylogeny of herpes viruses and other DNA viruses in that porcine pseudorabies virus α4 can substitute for human herpes simplex virus α4 as well as adenovirus E1a. Although not yet shown to function in bacteria, α4 is a well characterized DNA binding protein that binds the sequence 5'-ATCGTCNNNNYCGRC-3', SEQ ID NO: 3. The tet gene of pBR322 fortuitously contains two strong α4 binding sites located between +98 and +146 and between +179 and +227 nucleotides in the tet gene. Bacteria expressing α4 protein have been constructed. Tetracycline sensitivity upon induction of α4 gene expression is expected for this strain.

Bacteria will be isolated that grow in the presence of tetracycline and express α4 protein (α4/tet). The α4/tet bacteria will be plated in tetracycline-containing media under conditions where the α4 gene is induced. It is contemplated that rare Tet$^r$ mutants will emerge and will be isolated. Since mutant selection is in antibiotics that require retention of both the α4 plasmid and the tet plasmid, it is believed that these mutants will include, for example, the following classes: mutants in the tet gene such that α4 no longer binds; mutants in the α4 gene such that it either no longer binds the tet gene or is no longer expressed; and, chromosomal mutations. Chromosomal mutations are expected to include, for example, mutants in tetracycline uptake or mutants producing inhibitors of α4 function. The present invention provides that plasmids from mutants in the tet gene that prevent α4 binding, and chromosomal mutations, will be isolated and used to transform naive bacteria and the resulting doubly transformed bacteria will then be tested for their sensitivity to tetracycline following induction of α4.

The present invention provides that chromosomal mutants will be tested for the production of potential inhibitors of α4 function. The mutants will be cured of their plasmids and their sensitivity to tetracycline will be determined. If the mutants are tetracycline sensitive, then they will be tested further for the production of inhibitors of the α4 protein. They can be tested in vivo by transforming the cured strains with the α4 and the tet plasmids and testing for tetracycline sensitivity, or in vitro by preparing extracts of the cured strains and measuring their effect on the binding of α4 to the tet gene in the gel electrophoretic mobility shift assay. The biochemistry of the isolated compounds will be pursued by standard techniques known to those skilled in the art.

Another preferred embodiment uses bacterial strains that possesses an antibiotic resistance gene containing DNA binding sequences recognized by medically important DNA binding proteins to detect and produce anti-cancer drugs. For example, the myc oncogene product appears to be important in the maintenance of the oncogenic state and many malignancies. Inhibitors of the myc oncogene product, a DNA binding protein, are likely to be of chemotherapeutic value. The methods of the present invention can be easily adapted for the detection of myc inhibitors and subsequent generation of inhibitors by the mutant selection method. Briefly, the logic and methods described above for α4 are customized for myc. To customize the invention for myc, the DNA binding site recognized by myc is inserted into the tet gene in the promoter regulatory domain or the structural gene. Bacteria carrying this modified tet gene are transformed with a plasmid that expresses the myc gene. These transformed bacteria are expected to be unable to grow in tetracycline unless myc is inhibited. The invention is thus modified for the pursuit of an anti-cancer drug.

The present invention also provides methods to detect inhibitors of proteins that bind to other proteins to find inhibitors of proteins, such as human papilloma virus E6 and E7 proteins which bind and inactivate tumor suppressor gene products, including retinoblastoma (Rb) and p53 proteins. Such inhibitors are of likely value in the treatment of many malignancies, since these anti-oncogene products are frequently deleted, mutated or interfered with in such disease states. In one such embodiment of the present invention, the protein combining site of the Rb or p53 protein is inserted into the reporter or selectable marker function, such as the tet protein. Bacteria or yeast are transformed with this altered tet gene, as well as the protein that binds to this protein binding site, such as the appropriate papilloma virus E protein gene (hereinafter referred to as "the challenger"). These microorganisms will be unable to grow in the selection when the modified tet protein is complexed to the challenger. These microorganisms will also be unable to turn color in the reporter media when the modified tet protein is complexed to the challenger. Inhibitors of the challenger can then be tested for by the methods described in this invention and described for the other examples.

Another embodiment of the present invention provides methods that comprise the HSV protein VP16 as the target for screening antiviral agents. VP16 is a regulatory function of HSV that activates transcription of other HSV genes. Although not essential, VP16 minus virus are growth impaired, suggesting that inhibition of this function might have therapeutic value. Constructs were prepared in which the activating domain of VP16 was fused to the DNA binding domain of the yeast Gal4 protein. This chimeric protein activated transcription of genes that possessed the Gal4 DNA binding site in yeast. That is, the activating domain of VP16 was functional. By placing toxin genes near the Gal4 DNA binding site, yeast bearing the Gal4VP16 chimera would have to inhibit the activation properties of the chimera to survive. Hence, it is believed that an assay for the inhibition of VP16 will be possible.

One embodiment of the present invention provides methods whereby the gene encoding the SV40 T-antigen can be placed in bacteria to screen for antiviral agents. Since T-antigen binds sequences at the SV40 origin of replication, these sequences can be placed near the control regions of the tet gene. It is believed that recombinant bacteria expressing T-antigen will show a T-antigen-specific sensitivity towards tetracycline, and drugs that inhibit T-antigen binding can be assayed by growth of the this strain in tetracycline.

It is also provided that a variety of different antibiotic resistant markers will be useful in the methods of the present invention. One skilled in the art will be able to determine the most effective system.

It is further provided that yeast cells will be useful in the methods of the present invention, although the selection system cannot depend upon the tet gene.

The present invention is further illustrated by the following examples, which are not intended to be limiting in any way.

EXAMPLES

Example 1

Bacterial Strains and Plasmids

E. coli strain HB101 and plasmid pBR322 were from Bethesda Research Laboratories. Plasmid pACYC-184 (Chang et al., J. Bacteriol., 1978, Construction and Characterization of Amplifiable Multicopy DNA Cloning Vehicles Derived From the P15A Cryptic Miniplasmid, 134:1141–1156) was obtained from M. Nonoyama. Plasmid pPolo (Korant, 1990, AIDS Research and Reference Reagent Program Catalog (January) p. 51., U.S. Dept. of Health and Human Services, Washington, D.C.) was obtained from Y.-S. E. Cheng, and was modified such that the remaining tet homologous DNA has been deleted. All bacterial transformations were performed by the RbCl technique (Maniatis et al., 1982, Molecular Cloning: A Laboratory Manual, Cold Spring Harbor Lab., Cold Spring Harbor, N.Y.).

Example 2

Chemicals and Restriction Enzymes

Pepstatin A, ampicillin, chloramphenicol, tetracycline, and tryptophan were obtained from Sigma Chemical Co. Casamino Acids, yeast extract, and tryptone were from Difco Laboratories. Dimethyl sulfoxide was from Mallinckrodt. The synthetic oligonucleotides were synthesized on a Dupont Coder 300 and were isolated according to the instructions of the manufacturer. All restriction enzymes and T4 polynucleotide kinase were from Bethesda Research Laboratories and were used according to the instructions of the manufacturer.

Example 3

Construction of the Tet Protein Containing an HIV Protease Cleavage Site

Site-specific mutagenesis of the tet gene of pBR322 was performed as depicted in FIG. 1. The two synthetic 24-mers were mixed together and phosphorylated with T4 polynucleotide kinase. After hybridization, the 24-bp synthetic oligonucleotide fragment that encodes the HIV protease recognition sequence was inserted into the SalI site of pBR322, destroying the SalI site, but providing a new PvuI site. Recombinant molecules were transformed into E. coli HB101, and transformants were selected for ampicillin resistance and screened for resistance to tetracycline. Recombinant plasmids were identified by restriction enzyme analysis by using SalI and PvuI. Multiple insertions would result in the formation of a BstEI site, and none was detected. The resulting modified tet gene was then subcloned on the 1.4-kb HindIII-AvaI fragment into pACYC-184, replacing the resident tet gene to obtain a plasmid that has distinct drug resistance markers and is compatible with the HIV protease expression vector (pPolo). This new construct containing the Tet protein with the HIV protease site is called pACYC-10B3.

Example 4

Construction of a Strain That Requires the Inhibition of the HIV Protease for Growth in Tetracycline pPolo was selected as the source of HIV protease activity since it contains the HIV protease gene as a pol-pro precursor under the control of the E. coli tryptophan (trp) promoter. HB101 containing pPolo was transformed with either pACYC-184, containing wild-type tet gene, or pACYC-10B3, containing modified tet gene. Transformants were selected simultaneously for chloramphenicol resistance (pACYC-184) and ampicillin resistance (pPolo). Twenty-five independent transformants containing pPolo and either the wild-type (TJU524) or modified (TJU525) tet gene were tested for growth under conditions under which the protease was either expressed or repressed. Since the HIV protease is under the control of the trp promoter, it is constitutively expressed in bacteria grown in media lacking tryptophan and is repressed in the presence of tryptophan. Colonies were replica plated onto chloramphenicol-ampicillin plates or onto chloramphenicol-ampicillin-tetracycline plates with or without tryptophan. There was no apparent difference in the growth of TJU524 on ampicillin-chloramphenicol plates or ampicillin-chloramphenicol-tetracycline plates with or without tryptophan. Thus, the wild-type tet gene confers resistance to tetracycline whether or not the HIV protease is expressed. Transformants containing both pPolo and the modified tet gene (TJU525) grew vigorously on ampicillin-chloramphenicol plates. However, each of the 25 independent isolates failed to grow when exposed to tetracycline under conditions under which the HIV protease was expressed. The addition of tryptophan to inhibit the transcription of the HIV protease restored the growth of these isolates in the presence of tetracycline. Since the modified Tet protein confers resistance to tetracycline in the absence of the HIV protease and since tryptophan does not interfere with the toxicity of tetracycline, these results provide strong genetic evidence that the growth in tetracycline of bacteria containing both the HIV protease and the modified Tet protein is dependent upon the inhibition of the HIV protease.

Example 5

Tetracycline Susceptibility Curve

Figure 3:
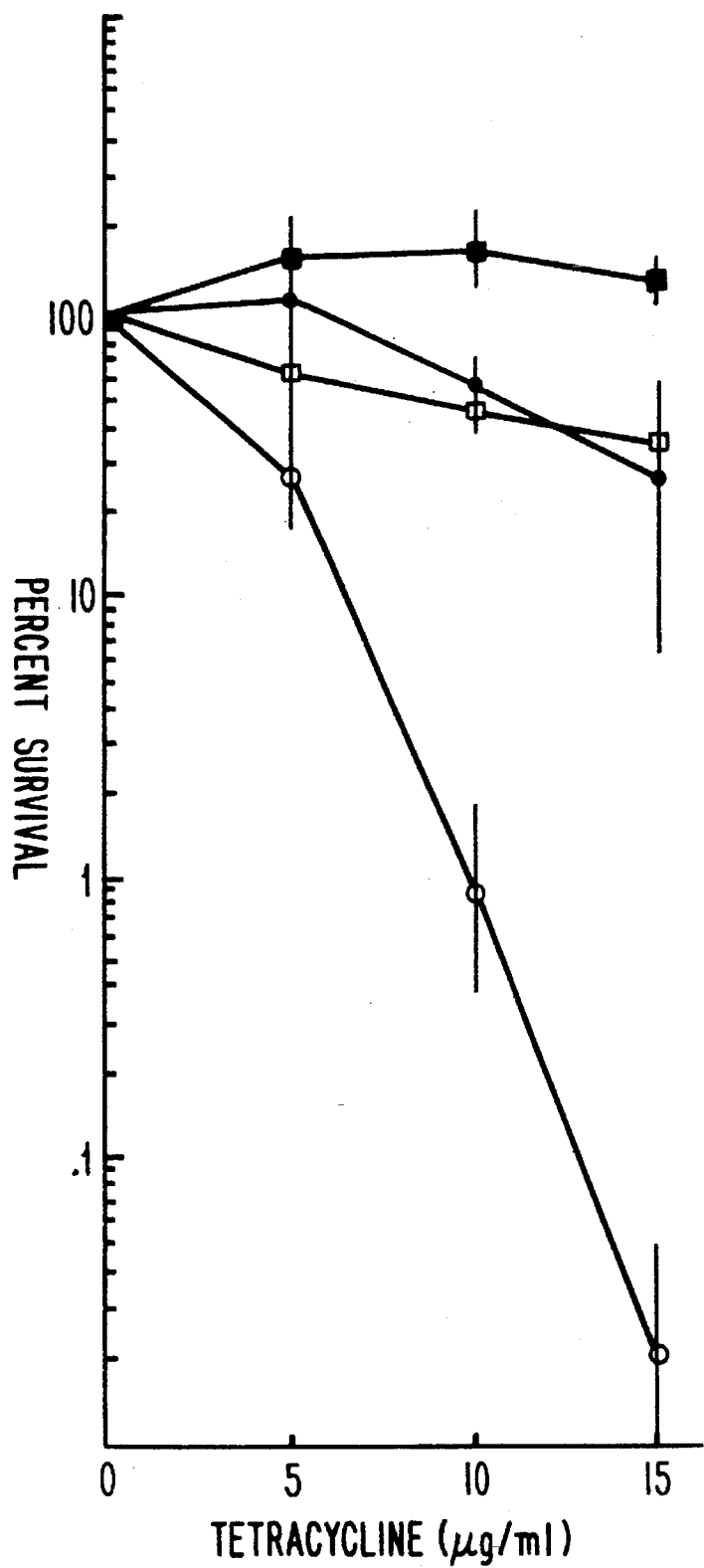
FIG. 3 is a tetracycline killing curve of bacterial strains containing the HIV protease and either the wild-type (TJU524) or modified (TJU525) Tet proteins. Exponentially growing bacteria were diluted and plated on M9 minimal medium agar with or without tryptophan and increasing concentrations of tetracycline. Survival on the plates containing no tetracycline was determined to be 100%. Circles, TJU525; squares, TJU524; open symbols, without tryptophan; filled symbols, with tryptophan. The lines through the symbols indicate standard deviations.

To quantitate the relative resistance to different tetracycline concentrations, the survival of exponentially growing TJU524 or TJU525 was analyzed in the presence of increasing concentrations of tetracycline in the absence and presence of tryptophan (FIG. 3). TJU525, which contained both the modified Tet protein and the HIV protease, exhibited an acute susceptibility to tetracycline, showing nearly $10^3$-fold fewer colonies in the presence of 15 µg/ml of tetracycline. This susceptibility was almost completely reversed when the expression of the HIV protease was inhibited by tryptophan. TJU524, which contained both the wild-type tet gene and pPolo, showed only 40% fewer colonies in the presence of 15 µg/ml tetracycline. However, this minor susceptibility was reversed when the bacteria were grown in the presence of tryptophan. The wild-type Tet protein of pBR322 has the sequence Cys-Met-Ala-Phe-Pro, SEQ ID NO: 4, between nucleotides 985 and 999, which could be a minor HIV protease recognition site. Although there are other explanations for the susceptibility of the strain containing the wild-type Tet protein to the expression of the HIV protease, one possibility is that the wild-type Tet protein is partially sensitive to cleavage by the HIV protease. Thus, the wild-type Tet protein exhibits only a modest degree of protease-dependent sensitivity when compared with the Tet protein containing the HIV protease recognition sequence. These results confirm that in doubly transformed cells, the modified tet gene confers resistance to tetracycline only when the expression of HIV protease is inhibited.

Example 6

Effect of Pepstatin A on Growth in the Presence of Tetracycline

Figure 2:
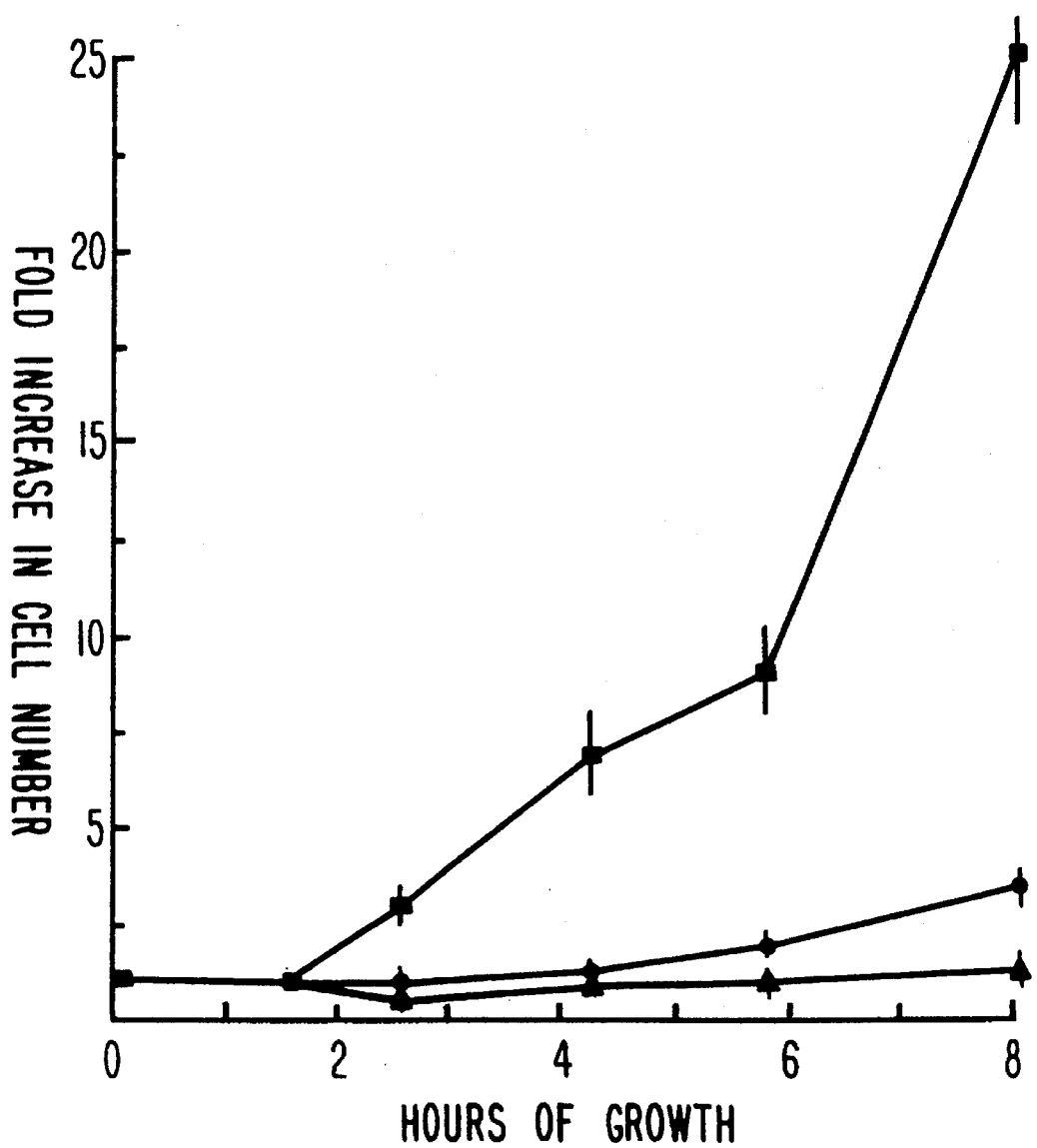
FIG. 2 is a graphical depiction of the growth of TJU525 in pepstatin A, an inhibitor of the HIV protease. TJU525 was grown in M9 minimal medium supplemented with either ampicillin-chloramphenicol (■) or ampicillin-chloramphenicol-tetracycline with (○) or without (△) pepstatin A. Growth is expressed as the fold increase in total bacterial number relative to the number of bacteria present at time zero. The lines through the symbols indicate standard deviations.

The utility of the invention for testing for inhibitors of the HIV protease was demonstrated by using pepstatin A, a known inhibitor of the HIV protease, which is also a member of the aspartate protease family and is inhibited in vitro by millimolar concentrations of pepstatin A. Since pepstatin A does not enhance the growth of HB101 in tetracycline, any improvement in the growth of TJU525 in tetracycline plus pepstatin A is attributable to inhibition of the HIV protease. As expected, there was no detectable growth of TJU525 in tetracycline (FIG. 2). However, the addition of 5 mM pepstatin A increases the growth rate in tetracycline 10 to 20% of that in the absence of tetracycline. Complete restoration of growth was not expected since HB101 carrying just the plasmid with the modified Tet protein yielded only 50% survival in the presence of 10 µg of tetracycline per ml. Since there was no detectable growth in the presence of tetracycline unless pepstatin A was added, the increase in the rate of growth owing to the presumed inhibition of the HIV protease by pepstatin A could not be calculated (division by zero). However, although cell survival (FIG. 3) and the rate of growth (FIG. 2) are different properties, a comparison is still informative. Thus, in the case of TJU525, there were 500-fold more colonies when the expression of the HIV protease was inhibited (FIG. 3). The inhibition of the protease by pepstatin restored the rate of growth to 10 to 20% of that seen in the absence of tetracycline (P 0.01, Z test). These results show that pepstatin A restored the growth of TJU525 nearly 100-fold (FIG. 2). Furthermore, after longer periods of incubation, no growth would be found in the presence of tetracycline alone, while the addition of pepstatin A would result in continued growth. These results provide additional evidence that TJU525 grows only in the presence of tetracycline if the HIV protease is inhibited.

Example 7

Co-cultivation Assay to Study and Identify HIV Protease Inhibitors

TJU525 is valuable as a screen for the identification of inhibitors of the protease, however, the analysis was limited to the verification of the assay with the use of Pepstatin A, a known inhibitor of HIV protease. TJU525 does not grow in tetracycline containing media since its Tet protein is cleaved by the protease. This allows for the genetic selection of rare mutants that have regained the ability to grow in tetracycline. Among these Tet resistant mutants would be ones that have reverted the protease site within our modified Tet protein. Other Tet resistant mutants could have inactivated the protease. It is also possible that among these Tet$^r$ mutants are ones that themselves are producing inhibitors of the protease. In this latter category are E. coli mutants that might degrade the HIV protease, block its expression, or ones that make a protein that complexes with the protease and forms an inactive complex. An example of mutants that block the expression of HIV are over-producers of tryptophan. In addition, it could be possible to generate Tet mutants that would make a low molecular weight inhibitor of the protease. Both the Lac and Trp repressors are just two well known examples of a strategy whereby E. coli uses low molecular weight effector molecules to greatly alter protein activity. It is this last class of mutants that could provide a innovative class of antiviral agents or furnish a model compound for the design of an effective antiviral agent. The difficulty, is a mechanism by which to distinguish between each of these different classes of mutation.

As mentioned above, a valuable mutant for chemotherapeutic purposes is the one that could be producing an inhibitor of the protease. The difficulty is to determine which of the mutants might be in this category, and to identify it among other mutants such as those which have reverted the tet gene or have inactivated the protease. Thus, methods for the genetic determination of such mutants are provided. Plasmids were isolated from 20 Tet$^r$ mutants and re-transformed into naive HB101. Transformants were selected for ampicillin and chloramphenicol resistance and screened for Tet resistance. From the original 20 Tet$^r$ mutants, only one had plasmids that conferred tetracycline resistance. These results indicate that the plasmids isolated from the other 19 Tet$^r$ mutants were not altered, and suggest that the original mutations which conferred resistance to tetracycline were the result of a chromosomal mutation. This is probably due to the fact that both the HIV protease and the Tet protein are on multicopy plasmids, and it would be rare to identify a mutation in these plasmid genes. These results suggested that plasmid derived mutants would not present a major difficulty in the screen.

To exploit the power of *E. coli* genetics an in vivo co-cultivation assay for the initial characterization of Tet resistant mutants to identify those that might be producing potential inhibitors of the HIV protease was designed. First, a new tester strain that would contain the HIV protease and the target Tet protein in a Lac-background (JM109) was constructed. On IPTG/X-gal plates, this strain (RG539) is white, whereas the tester strain (RG533) in HB101(Lac+) is blue. Tet resistant mutants are putative synthesizers of an HIV protease inhibitor. Therefore, Tet resistant mutants were selected on tetracycline plates using strain RG539. The resulting mutants (Tet$^r$, white) were screened for the synthesis of an inhibitor of the HIV protease using a co-cultivation assay with the original tester strain RG533 (Tet$^s$, blue). Only Tet$^r$ colonies that secrete an inhibitor of the HIV protease, or somehow interfere with tetracycline uptake, will allow the tetracycline sensitive test strain to grow. 20 such Tet$^r$ mutants able to restore the Tet$^s$ tester colonies to growth have been identified.

One such Tet$^r$ mutant that could be elaborating an inhibitor of the HIV protease was characterized further. This mutant (#11) was isolated after five days of selection in tetracycline. Growth of the blue Tet sensitive tester colonies is readily seen on the white background of the Tet resistant mutant. These blue colonies have been isolated and are still Tet sensitive, consistent with the idea that either an inhibitor of the protease is being produced or that the effectiveness of tetracycline has somehow been reduced. Mixture of mutant #11 with a blue, Tet sensitive strain lacking the HIV protease yields no blue colonies. These results suggest that the growth of the blue colonies is not due to the degradation, or other effect, of tetracycline in the plates. JM109 containing pBR325 (Tet$^r$) was mixed with HIV protease Tet sensitive tester strain to demonstrate that the growth of the blue tester colonies is not a result of plasmid mediated tet resistance gene. The Tet resistant mutant is also plated by itself demonstrating that no reversion from Lac– (white) to Lac+ (blue) colonies had occurred. These results are consistent with the Tet$^r$ mutant colony producing and secreting an inhibitor of the HIV protease.

Since mutant #11 has the genetic properties of a bacteria that is producing and secreting an inhibitor of the HIV protease, samples were prepared to test for the presence of the putative inhibitor. Media from overnight cultures of the bacteria were tested for the presence of an inhibitor by assaying for protease activity using the purified HIV protease and an undecamer peptide, substrate III, obtained from Bachem Bioscience, Philadelphia, Pa. Reaction products were separated and quantified by HPLC analysis as directed the supplier of substrate III. In the absence of Pepstatin A, there is a 60% cleavage of substrate III (s) into the carboxy (c) and amino (n) terminal peptides. In the presence of Pepstatin A, this reaction is inhibited by 90%. In each case there is no detectable inhibition of the HIV protease (58% and 59% digestion, respectively). However, in the case of mutant #11, an additional peak is present that is not observed in the wildtype assay. To test whether or not this new peak was the result of degradation by the protease, the media from either mutant #11 or wildtype were chromatographed without prior enzyme treatment. This new peak is not the result of HIV protease degradation, but is only found in the media from mutant #11, and not in the parent strain. Upon further analysis, this peak was identified as tryptophan. That is, mutant #11 is Tet$^r$ because it inhibits the expression of the HIV protease through the production of tryptophan since the protease is under the regulation of the Trp promoter. Presumably, this is a cis mutation in the operator of the Trp operon that prevents the Trp repressor from binding and allows the overproduction of tryptophan which can then activate the Trp repressor and turn off the transcription of the protease. Of the 20 mutants identified as allowing the HIV protease strain to grow in the co-cultivation assay, 19 have tryptophan in the media and are presumably this class of mutation. One of the mutants generated does not conform to any known mutation and is being characterized further since it is possibly elaborating an HIV protease inhibitor. These results demonstrate that embodiments of the invention are useful for generating expected mutants as well as surprising, potentially novel mutants.

Example 8

Determination if tet-x Can Serve as Substrate for hbx

The hbx gene, derived from woodchuck hepatitis virus, was cloned into a plasmid. The PBR322 tetracycline gene has been modified to contain the 7 amino acid sequence designed to be recognized by the hbx gene product. The modified tet gene is called tet-x and confers tetracycline resistance to sensitive strains. Therefore, the insertion of these amino acids into the tet gene in frame does not eliminate Tet function. The modified protein elaborated by this gene is called Tet-x. The tet-x and hbx genes have been molecularly cloned into *E. coli* strain JM109. The doubly transformed strain is called TJU-hbx:tet$^x$. Since the basis of these experiments requires that Tet-x be modified by hbx, it will be important to determine if Tet-x is a substrate for hbx kination. Preliminary experiments indicate that the Tet-x can undergo kination at serine residues, as anticipated by design. Direct identification of kination will serve two functions. First, it will confirm that hbx is, as expected, functional as isolated from bacteria as a protein kinase. Second, it will provide biochemical evidence that the tet-x protein behaves as expected. Further, hbx and kinase assays will also be performed. Tet-x will be prepared by in vitro transcription and translation reactions. Specificity of the reactions will be monitored by use of wildtype tet protein as substrate. Since wildtype tet does not contain the amino acid sequences predicted to be kination sites for hbx, wild type tet should not be an efficient substrate.

Example 9

Figure 4:
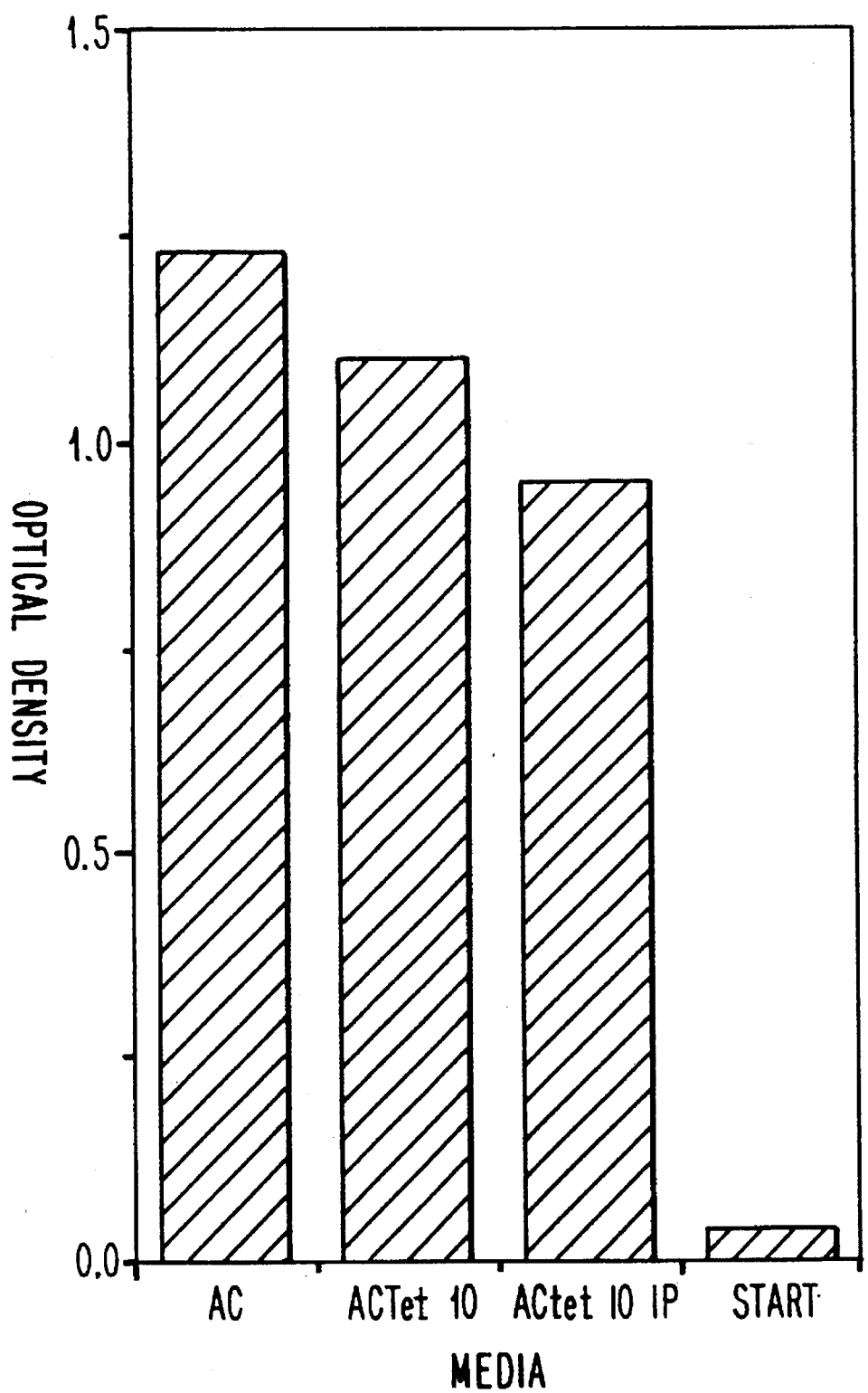
FIG. 4 is a graphical depiction of the growth of TJU-hbx:$tet^x$ in Tet media when the x gene is induced with IPTG. TJU-hbx:$tet^x$ is a JM109 strain containing plasmids pACYC-184, which is a source of the tet gene and chloramphenicol resistance, as well as pWhx, the woodchuck hepatitis virus x gene containing plasmid which confers resistance to ampicillin. AC, Ampicillin and chloramphenicol; Tet 10, 10 μg./ml. tetracycline; IP, 160 μM IPTG. Start: refers to the initial OD (590) of the cultures.
Figure 5:
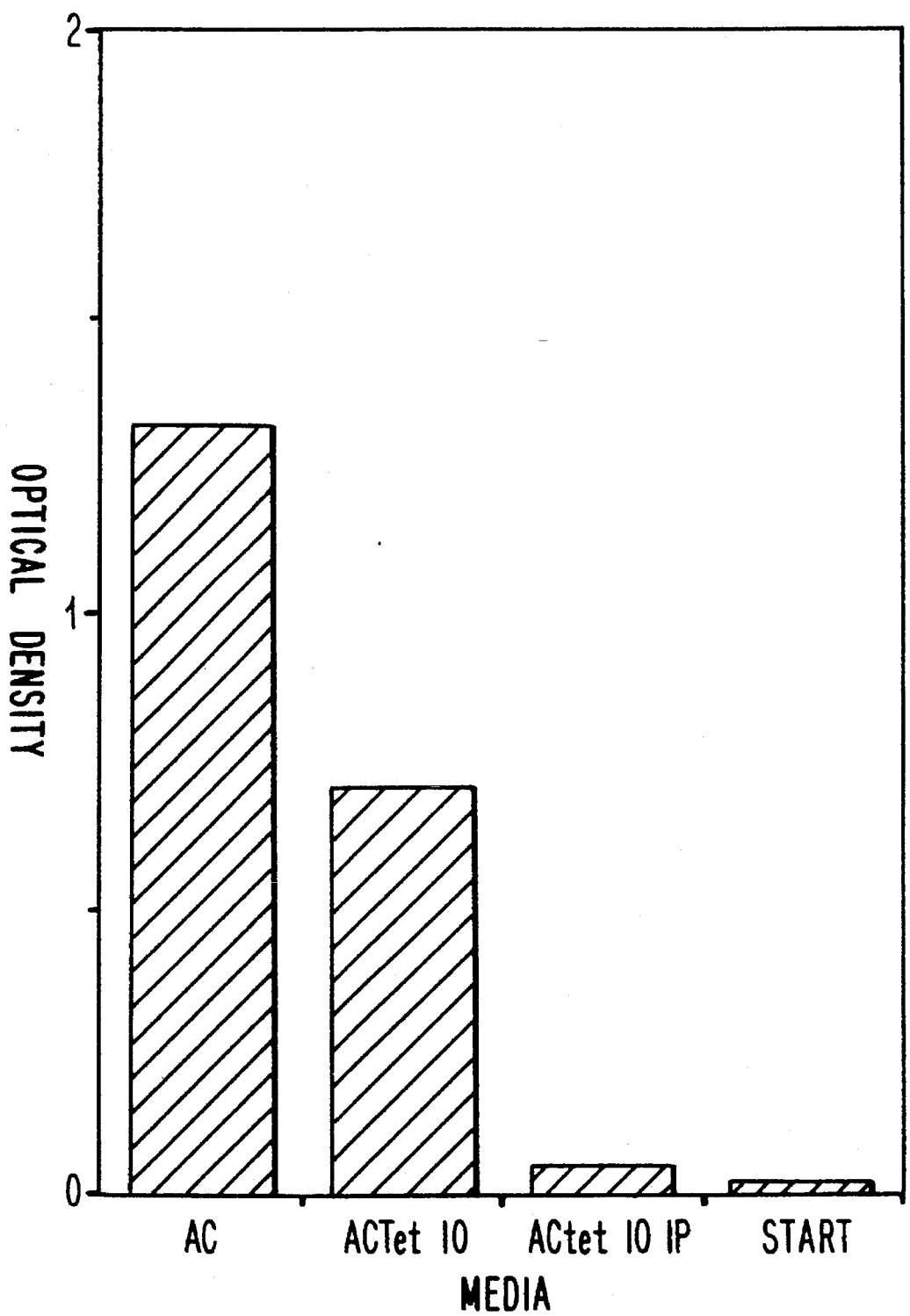
FIG. 5 is a graphical depiction of the growth of TJU-hbx:$tet^x$ in Tet media when the whx gene is induced with IPTG. TJU-hbx:$tet^x$ is a JM109 strain that contains plasmids pACYC-184:$tet^x$, which is the source of both the modified tet gene containing the putative x kinase recognition site and the chloramphenicol resistance gene. The strain also contains pWhx as described in FIG. 5. Abbreviations are as described in FIG. 5.
Figure 6:
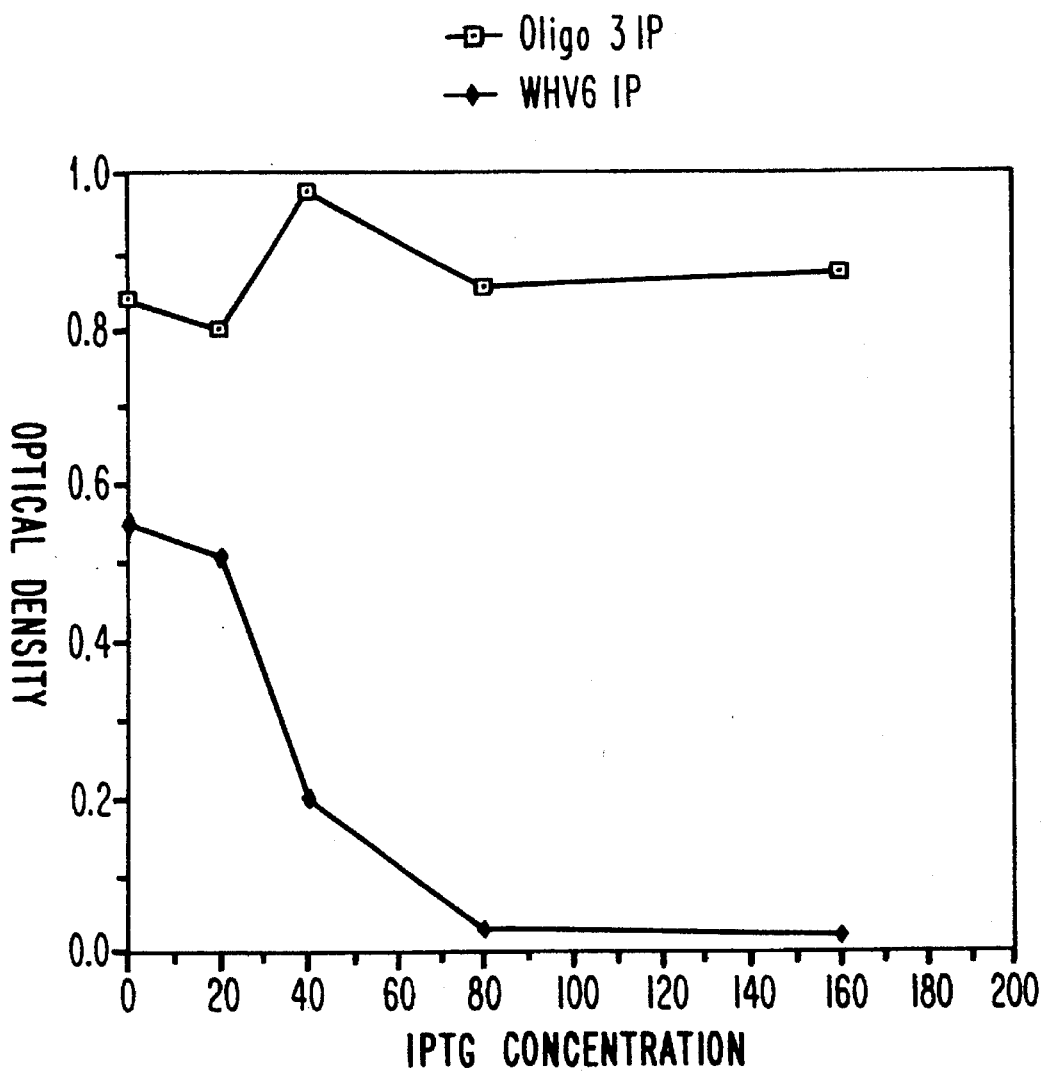
FIG. 6 is a graphical illustration of the IPTG sensitivity of TJU-hbx:$tet^x$. IPTG is an inducer of x gene expression. Oligo 3 is not sensitive to IPTG induced expression of the x gene. Cultures were seeded at an initial OD (590) of 0.02 and incubated in growth media containing the indicated concentration of IPTG for five hours. Final OD (590) readings are presented as a measure of bacteria growth. Oligo 3 is a JM109 derived strain that contains pACYC-184:$tet^x$, but no whx gene.

Examination of Growth of TJU-hbx:tet$^x$ in Tetracycline Media and Dependence Upon the Inhibition of hbx Having produced the relevant strains and demonstrated that Tet-x is, indeed, subject to kination by hbx, it is expected that a bacteria strain such as TJU-hbx:tet$^x$, which expresses both hbx and tet-x will unable to grow in tet media when the hbx gene is induced. Further, it is expected that growth in tetracycline media will be restored by repression of hbx. It has been shown that *E. coli* expressing both hbx as well as the wildtype tet protein are as viable and grow vigorously in tetracycline media as do strains that lack hbx. In these strains hbx is expressed to as much as 0.5% of total protein mass. It is clear that expression of hbx, per se, at these levels is not growth inhibitory. Thus, any growth sensitivity of TJU-hbx:tet$^x$ tetracycline media under conditions where the hbx gene is induced will be considered evidence that the bacteria can not grow because hbx is modifying Tet-x. FIGS. 4 through 6 demonstrate that TJU-hbx:tet$^x$ does not grow in tetracycline containing media when the hbx gene is induced. Control experiments, using bacterial strain Oligo 3, which contains a modified tet-x gene but no x gene, show bacterial growth under IPTG induction.

These experiments will be conducted over a range of tetracycline concentrations and levels of hbx induction. The level of hbx induction and phosphorylation status of Tet-x will be biochemically determined by kinase assays and SDS gel electrophoresis. Control kinase experiments will be carried out on wild type Tet in control strains. It is expected that Tet-x, as isolated from bacteria, will be phosphorylated in response to hbx induction and the cells will be unable to grow in tetracycline. This will be determined directly by phospho-amino acid analysis. Similarly, it is expected that wild type Tet will remain unphosphorylated or incompletely phosphorylated, as isolated from bacteria induced for hbx, and that these bacteria will grow vigorously in tetracycline media. Preliminary results suggest that these expectations are correct. It is therefore believed that it is possible to construct tet-x/hbx expresser strains whose growth depends, at least phenotypically, upon repression of the hbx.

Example 10

Construction of HSV α4 Expression Vectors

The effects of the expression of α4 on *E. coli* growth will be determined. If the overexpression of α4 is toxic to bacteria, then other expression vectors will have to be made. The Excalibur vector (Ivanoff, L. A. et al. *Proc. Natl. Acad Sci. U.S.A.* 83:5392–5396 (1986) used for HIV protease expression is expected to be useful in these experiments since it is regulated by tryptophan. In addition, the α4 gene can be placed under the control of the Lac repressor or on a low copy number plasmid. The lethality of α4 could provide an antiviral assay and be useful in the selection of both α4 mutant proteins as well as potential host mutants that might be synthesizing novel inhibitors.

Since α4 is an unspliced gene, an HSV1 genomic BstEII fragment containing the entire α4 gene will be inserted into pGem4Z placing the α4 structural gene within 40 nucleotides of the T7 RNA polymerase promoter. The α4 gene includes a ribosome binding site adjacent to the first AUG. The plasmid will be placed in the appropriate host containing an inducible T7 RNA polymerase gene. Similar constructs will be made with a mutant α4 gene (α4mt), which codes for a protein unable to bind DNA. Following induction of T7 RNA polymerase, the α4 protein will be identified by its mobility in SDS-PAGE, followed by immunoprecipitation with polyclonal antibody of the α4 protein isolated from bacterial extracts. The isolated proteins will be tested for DNA binding activity to determine if the recombinant α4 recognizes the appropriate DNA sequence.

Example 11

Binding of α4 Produced in Bacteria to the α4 Consensus Sequence

To determine if α4 protein produced in *E. coli* can bind DNA with the same specificity of the viral protein, recombinant α4 will be purified and tested for its ability to bind unique DNA fragment with and without the consensus sequence in the gel electrophoretic mobility shift assay. (Faber, S. W. and Wilcox, K. W. *Nucl. Acids Res.* 16:555–570 (1983)). The DNA binding will be compared to α4 derived from infected mammalian cells. It is expected that the bacterial α4 will bind the sequence. If bacterial α4 binds the consensus sequence the methods of the invention will be carried out in bacteria. If it does not, the possibility that α4 requires modification not provided by *E. coli* will be considered. In this case, other hosts or other DNA binding proteins will be used for the methods of this invention. It is expected that yeast will be useful in these methods.

Example 12

Transformation of the Strain Containing the α4 Plasmid With pBR322 tet Gene

If α4 produced in *E. coli* binds DNA specifically, transformants that express either functional or mutant α4 (α4mt) will be used as hosts for receiving the pBR322 tet gene. Since pACYC-184 and pBR322 have identical tet genes, pACYC-184 will be used as the source of the tet gene because of its compatibility with the pGem4Z (pBR322) origin of replication. Transformants will be selected simultaneously for chloramphenicol (pACYC-184) and ampicillin (pGEM4Z) resistance. Double transformants will be isolated and will be used in further studies.

Example 13

Tetracycline Resistance Profile of Double Transformants Containing the HSV α4 Gene: Growth With or Without α4 Induction The methods of the invention will be tested with bacteria that express functional or mutant α4 and contain the tet gene. The α4/tet strain contains a wildtype copy of the α4 gene and a tet gene. The α4mt/tet strain contains the mutant α4 gene and a tet gene. The growth of other bacteria in tetracycline containing media under conditions where the α4 protein is made will be examined. Bacteria will be grown in media containing increasing concentrations of tetracycline in the absence and presence of various levels of induction of α4 gene expression. Bacterial growth will be determined in liquid culture by standard analysis. There are several likely results seen using α4/tet and α4mt/tet bacteria under conditions where the α4 gene has been induced. For example, bacteria that express functional α4 have an increased sensitivity to tetracycline while those that express α4mt will have wildtype resistance to tetracycline when compared to pBR322 transformed bacteria that lack an α4 protein. If the binding of α4 to the tet gene does not interfere with transcription, then both strains of bacteria may possess a wildtype resistance to tetracycline. Moreover, the combined effect of expression of the α4 protein and the exposure to tetracycline may be toxic to the cells independent of DNA binding.

Bacteria expressing functional α4 will not grow in tetracycline containing media. In this case, bacteria expressing α4mt/tet will serve as a genetic control. It is predicted that these bacteria will grow in tetracycline containing media. In addition, Tn10, which does not contain the α4 consensus sequence, can serve as an alternative source of the tet gene. In this case, tetracycline resistance will be independent of the expression of α4.

If the in vitro studies indicate that α4 does not block transcription of the tet gene, then it will then be necessary to make modifications. For example, additional α4 binding sites may be added to the tet gene immediately upstream of the RNA polymerase binding site or within the 5' untranslated portion of the gene.

Example 14

Creation of Bacterial Strains Expressing HBV Pol And Core Proteins

The present invention includes a bacterial strain whose growth in tetracycline media requires that the packaging function of HBV pol and core proteins be inhibited. Bacteria have been constructed that possess a tetracycline resistance mRNA gene product that contains the 64 nucleotide packaging site recognized by HBV pol and core gene products. This *E. coli* strain has been designated TJU-etet-pol/core. It is believed that when this bacteria expresses an appropriate amount of HBV pol and core gene product, the tet mRNA will become complexed with pol and core protein and be unable to become translated into tet protein. Bacteria will be unable to grow in tetracycline media when core and pol are functional. Preliminary results using TJU-etet-pol/core suggest that this strain can not grow in tetracycline containing media when core and pol proteins are made. Therefore, inhibitors of HBV packaging can be screened for by the co-cultivation methods outlined above: compounds are tested for anti-packaging activity by testing their ability to enhance the growth of this bacteria in tetracycline media. Moreover, mutant bacteria can be selected for by plating the bacteria in tetracycline media and selecting rare isolates. These rare isolates may include mutant bacteria that produce inhibitors of HBV packaging. These mutants can be distinguished from the other kinds of mutants that may occur by the methods and logic outlined above. Briefly, they are first tested for the presence of plasmids with the original tet and core and pol genotypes. If they have the original core and tet and pol genotypes, they will be tested further for the possibility that they are producing inhibitors of packaging by testing bacterial extracts for their ability to inhibit of HBV by conventional mammalian tissue culture assays.

Example 15

Method For Screening and Identifying Drugs That Inhibit Renin, Angiotensin Converting Enzyme And Kinins A method is also provided to screen for and identify drugs that inhibit renin, angiotensin converting enzyme (ACE) and kinins. Renin and ACE inhibitors will be of value in the control of hypertension. Kinin inhibitors will presumably have antiinflammatory activity.

Kinins such as bradykinin are polypeptide vasodilators and are mediators of inflammation in people. Inhibition of kinin production in the human body is likely to be of great value in the management of inflammatory responses, which are often of grave consequence. Kinins are produced in the body by the proteolytic cleavage of precursor proteins called kininogen. Kininogen is cleaved between the amino acids methionine and lysine and arginine and serine and arginine by the protease kallikrein to form the vasoactive produce, kinin (bradykinin) (Ganong, W. F., *Review of Medical Physiology*, p. 504, Appleton and Lange (1989)). Therefore, the inhibition of the human protease, kallikrein, would prevent bradykinin formation and have antiinflammatory value.

Bradykinin is produced in the human body when the protease, kallikrein cleaves kininogen at the 11 amino acid sequence: Met-Lys-*-Arg-Pro-Pro-Gly-Phe-Ser-Phe-Arg-*-Ser-Val-, SEQ ID NO: 5, where the asterisks indicate the cleavage sites. Amino acid abbreviations are as follows: Met, methionine; Lys, lysine, Arg, arginine; Pro, proline; Gly, glycine; Ser, serine and Val, valine.

The tetracycline gene of *E. coli* plasmid pBR322 (tet gene) mediates resistance of the bacteria *E. coli* to tetracycline. Inventors have shown that the tet gene can tolerate insertions of up to 8 amino acids and remain functional. Moreover, insertions of appropriate amino sequences into the Tet gene protein results in a protein that became a substrate for proteases that cleave proteins at those amino acid sequences.

Therefore, a bacterial system for the detection and generation of inhibitors of the protease kallikrein can be constructed by molecularly cloning a seven amino acid sequence that specifies the amino acid cleavage sites for kallikrein. In particular, the DNA specifying the following amino acid sequences can be cloned into the SalI site of the Tet gene. This is the same restriction site used to introduce insertions of protease recognition signals: (Recognition Site I) Met-Lys-*-Arg-Pro-Pro-Gly-Phe, SEQ ID NO: 6, and (Recognition Site II) Pro-Gly-Phe-Ser-Phe-Arg-*-Ser-Val, SEQ ID NO: 7. It is proposed that two separate modified Tet gene constructs will be made. One Tet construct will have the Recognition Site I and the other will have the Recognition Site II.

The modified tet genes will be called tet-kin-I and tet-kin-II, respectively, and will be contained on plasmid pACYC-184, which confers chloramphenicol and tetracycline resistance to *E. coli*.

The gene for the appropriate tissue or plasma kallikrein which has been molecularly cloned will be molecularly cloned into the plasmid P-Polo under the control of the tryptophan promoter, as was the HIV protease. This plasmid confers ampicillin resistance to *E. coli*.

Doubly transformed *E. coli* will be made, which contain a modified tet gene, on plasmid pACYC-184, and a kallikrein gene, on plasmid P-Polo lacking the HIV protease gene. These doubly transformed mutants will be selected by growth in chloramphenicol and ampicillin. Such doubly transformed bacteria will be called tet-kin/amp-kal. tet-kin/amp-kal bacteria will grow in ampicillin and chloramphenicol media. However, its growth in tetracycline media will depend upon the inhibition of the protease kallikrein, since the tetracycline resistance protein cloned into this strain is cleaved by kallikrein in to inactive fragments.

Therefore, inhibitors of kallikrein can be screened by a simple bacterial growth assay, as was described and used for the detection of inhibitors of the HIV protease.

Similarly, mutant tet-kin/amp-kal bacteria which may be producing inhibitors of the kallikrein protease can be selected for by plating the bacteria on tetracycline containing media under conditions where the kallikrein protease is induced in the absence of tryptophan. Rare mutants arise which have gained the ability to grow in tetracycline even though the kallikrein protease is expressed and its Tet protein is a substrate for kallikrein cleavage. The mutants of interest are characterized as was done for the HIV protease system in the examples above.

Example 16

Construction of Bacteria That Require Renin or Angiotensin Inhibition to Grow in the Presence of Tetracycline An example is provided where bacteria are constructed that must inhibit renin (Construct 1) or angiotensin converting enzyme (ACE) (Construct 2) for their growth in tetracycline containing medium.

Renin and ACE are human proteases involved in the generation of the vasoconstrictors angiotensin II and III from angiotensinogen. Inhibitors of the formation of angiotensins, such as inhibitors of ACE, are of proven clinical value in the management of hypertension and congestive heart failure. The drug, Captopril™ (Squibb) is one such agent.

Renin cleaves angiotensinogen within the seven amino acid sequence: Phe-His-Leu-*-Leu-Val-Tyr-Ser, SEQ ID NO: 8. ACE, cleaves angiotensin I within the seven amino acid sequence: Tyr-Ile-His-Pro-Phe-*-His-Leu, SEQ ID NO: 9.

Bacteria which must inhibit the protease function of renin and bacteria which must inhibit the protease action of ACE for their growth in selective media will be constructed as follows:

For the bacteria which must inhibit renin, the DNA sequence specifying the seven amino acid sequence provided in Example 15, which is recognized and cleaved by renin, will be inserted into the PBR322 tetracycline gene, contained on the plasmid at the SalI site. pACYC-184 specifies resistance to chloramphenicol as well as tetracycline. The modified tet gene will be called tet-renin and specify a tet polypeptide gene product that is cleaved in to inactivity by the protease renin, based upon our previous studies of the tet gene.

For the construction of bacteria which must inhibit ACE, the DNA sequence that specifies the seven amino acids provided above, which is recognized and cleaved by the ACE, will be inserted into the SalI site of the tet gene, contained on plasmid pACYC-184. This modified tet gene is expected to produce a polypeptide product that is cleaved into inactivity by the action of the ACE protease and will be called tet-ACE.

The tet-renin gene will be transformed into one set of *E. coli* by selection for chloramphenicol resistance. This strain will be called tet-renin.

Another set of *E. coli* will be transformed to chloramphenicol resistance with the tet-ACE plasmid. This strain will be called tet-ACE.

The tet-renin bacteria will be further transformed with an ampicillin resistant plasmid that contains a function renin gene, under the control of the tryptophan promoter. These bacteria will be called tet-renin:renin.

The tet-ACE bacteria will be further transformed with a plasmid that specifies ampicillin resistance as well as the gene for ACE, under the control of the tryptophan promoter. This strain will be called tet-ACE:ACE.

The tet-renin:renin strain will be maintained on ampicillin: chloramphenicol containing media, but will be unable to grow in media containing tetracycline under conditions where the renin gene is induced, since renin will cleave the tet-renin polypeptide into inactivity, by proteolytic digestion at the seven amino acid sequence inserted into the modified Tet protein. Drugs that inhibit renin can be easily detected by their ability to enhance the growth of this strain in tetracycline media under conditions where the renin gene is induced. This is exactly the same methods described for the HIV protease system in the above examples. Mutants of this strain which may be producing inhibitors of the renin protease can be selected by plating the bacteria in tetracycline media and isolating rare mutants that have gained the ability to grow in tetracycline in spite of the fact that the renin protease is made. These mutants will be tested for the possibility that they are producing an inhibitor of the renin protease after testing the mutant bacteria for the presence of plasmids with the genotypes for the renin and tet genes originally used in the formation of the tet-renin:renin bacteria strain, using methods of the invention.

The tet-ACE:ACE strain will be maintained in ampicillin: chloramphenicol containing media, but will be unable to grow in tetracycline media under conditions where the ACE gene is induced because the ACE protease will proteolytically cleave the modified Tet protein (tet-ACE gene product). Drugs that inhibit ACE can be detected, as described above, by their ability to enhance the growth of the tet-ACE:ACE strain in tetracycline media under conditions where the ACE gene is induced. Mutants of this strain which may themselves be producing inhibitors of the ACE protease can be selected by plating the tet-ACE:ACE strain in tetracycline and isolating rare mutants which have appeared, in spite of the fact that the ACE protease is being made. These mutants will be tested for the possibility that they produce inhibitors of ACE after assessing the presence of the original plasmids used in the formation of this strain by a system identical to that described above for the HIV protease inhibitor screening.

While a number of specific embodiments have been set forth, the present invention is to be limited only in accordance with the following claims.

What is claimed is:

1. A method of identifying an inhibitor of a viral enzyme comprising:
   (a) providing a microorganism having a first expression vector encoding a viral enzyme and a second expression vector comprising a nucleotide sequence encoding a modified tetracycline resistance protein, said modified tetracycline resistance protein having a function which may be deactivated by said viral enzyme;
   (b) culturing the microorganism in a culture medium in the presence of test compound;
   (c) adding tetracycline to said culture medium; and
   (d) determining the activity of the modified tetracycline resistance protein function, thereby identifying an inhibitor of a viral enzyme.

2. The method of claim 1, wherein the microorganism is yeast or *E. coli*.

3. The method of claim 1, wherein the modified reporter protein is a modified antibiotic resistance protein and the selection agent is an antibiotic.

4. The method of claim 1, wherein the viral enzyme is a human immunodeficiency virus enzyme.

5. The method of claim 1, wherein the viral enzyme is HIV protease; and the modified reporter protein comprises the HIV protease recognition sequence.

6. The method of claim 1, wherein the HIV protease recognition sequence consists essentially of SEQ ID NO: 1.

7. The method of claim 1, wherein the viral enzyme is hepatitis B virus x kinase and the modified reporter protein comprises the x kinase substrate recognition sequence.

8. The method of claim 7, wherein the x kinase substrate recognition sequence consists essentially of SEQ ID NO: 2.

9. The method of claim 1, wherein the viral enzyme comprises hepatitis B virus core and pol protein and the modified reporter protein comprises the packaging recognition sequence.

10. The method of claim 37, wherein the packaging recognition sequence consists essentially of SEQ ID NO: 10.

11. The method of claim 1, wherein the viral enzyme comprises human papilloma virus E6 and E7 protein and the modified reporter protein is selected from the group consisting of the recognition sequence of Rb protein and the recognition sequence of p53 protein.

\* \* \* \* \*

UNITED STATES PATENT AND TRADEMARK OFFICE
CERTIFICATE OF CORRECTION

PATENT NO. : 5,532,124
DATED : July 2, 1996
INVENTOR(S) : Timothy M. BLOCK et al.

It is certified that error appears in the above-indentified patent and that said Letters Patent is hereby corrected as shown below:

At column 6, line 65, insert --for their medical potential by simply co-cultivating them-- after the word "tested";

At column 6, line 6, insert --only-- after the word "can";

At column 5, line 36, delete ":" after the word "inhibited.";

At column 15, line 38, delete "." before the word "exhibited";

At column 18, line 45, delete "-" between the words "functional" and "as";

At column 28, line 1 of claim 6, delete "1" and insert "5";

At column 28, line 1 of claim 10, delete "37" and insert "9".

Signed and Sealed this

First Day of October, 1996

Attest:

BRUCE LEHMAN

Attesting Officer     Commissioner of Patents and Trademarks